(12) United States Patent
Whitehead et al.

(10) Patent No.: US 7,754,198 B2
(45) Date of Patent: Jul. 13, 2010

(54) AROMA-RELEASING POLYMERIC GEL MATRIX

(76) Inventors: Kenneth R. Whitehead, 385 Farmhouse La., Wind Gap, PA (US) 18091; Ronald B. Smith, 806 Westridge Dr., Hockessin, DE (US) 19707

(*) Notice: Subject to any disclaimer, the term of this patent is extended or adjusted under 35 U.S.C. 154(b) by 843 days.

(21) Appl. No.: 11/291,818

(22) Filed: Dec. 2, 2005

(65) Prior Publication Data

US 2007/0128148 A1    Jun. 7, 2007

(51) Int. Cl.
A61L 9/00     (2006.01)
A61L 9/012    (2006.01)
A61L 9/013    (2006.01)
A61L 9/014    (2006.01)

(52) U.S. Cl. .................................... 424/76.4

(58) Field of Classification Search ............. 424/76.4
See application file for complete search history.

(56) References Cited

U.S. PATENT DOCUMENTS

| | | | |
|---|---|---|---|
| 3,182,035 A | | 5/1965 | Garman |
| 3,685,734 A | | 8/1972 | Paciorek et al. |
| 3,688,985 A | * | 9/1972 | Engel et al. ............. 239/54 |
| 3,725,311 A | * | 4/1973 | Grubb ..................... 512/4 |
| 4,889,755 A | | 12/1989 | Charbonneau |
| 5,603,925 A | | 2/1997 | Ross et al. |
| 5,723,420 A | * | 3/1998 | Wei et al. ............... 510/101 |
| 5,739,100 A | | 4/1998 | Horino et al. |
| 5,871,765 A | * | 2/1999 | Johnson et al. ......... 424/409 |
| 5,903,710 A | | 5/1999 | Weffler et al. |
| 6,460,464 B1 | | 10/2002 | Attarwala |

* cited by examiner

Primary Examiner—Johann R Richter
Assistant Examiner—Courtney Brown
(74) Attorney, Agent, or Firm—Louis C. Paul & Associates, PLLC

(57) ABSTRACT

A translucent-to-clear, plasticized PVC thermoplastic polymeric matrix gel composition comprising (i) a high loading of fragrance composition and/or odor counteractant(s)—preferably greater than about 85%; (ii) from about 4% to about 25% of a plastisol with a Shore hardness of from about 60 to about 95 that is liquid at room temperature; and, optionally, (iii) an evaporation/firmness controlling agent. The high loading of fragrance and/or odor counteractants in the polymeric matrix gel composition of the invention provides a desired aroma to an environment in a persistent manner over an extended period of time.

35 Claims, No Drawings

AROMA-RELEASING POLYMERIC GEL MATRIX

FIELD OF INVENTION

The present invention relates to a method of providing in a persistent manner a desired aroma to an environment from a clear to translucent, plasticized PVC thermoplastic polymer matrix that contains a high loading of fragrance composition and/or oil-soluble odor counteractant.

BACKGROUND

From the earliest recorded uses of perfumes by the ancient Egyptians, achieving a fragrant environment has long been a goal of man. Over the centuries, man's aversion to malodor has led to the development of a variety of products for "air freshening". These include potpourri, scented candles, aerosols and gels, each containing volatile fragrance and/or volatile odor counteractants.

Upon opening or activating an air freshener, volatile fragrances and/or volatile odor counteractants are released, masking unpleasant odors in the surrounding environment. As used in this application, the term "air freshening" means imparting a desired aroma to an environment and/or that odors in the surrounding atmosphere are masked by the volatile fragrance and/or volatile odor counteractants emitted from delivery system. Essential oils—concentrated, aromatic, volatile oils extracted from the flowers, leaves, stems, or roots that give plants their pleasing scents—are common ingredients in air freshening products. In many commercial air fresheners, essential oils are diluted with one or more carriers.

From a consumer standpoint, a need has existed, and continues to exist, for an environment that has a persistently pleasant, but not overpowering, aroma or fragrance. It has therefore been an objective of air freshener manufacturers to make products that provide a continuous, long-lasting release of a desired aroma to an environment to achieve a pleasant scent over an extended period of time. The difficulty in achieving this objective lies in the differing volatilities of the perfumery materials that make up the fragrance compositions and/or odor counteractants used in air fresheners. In order for fragrance compositions and/or odor counteractants to be effective, they must be volatilized—that is small and light enough to enter the nasal passage, be trapped by cilia and trigger one of hundreds of different olfactory receptors. However, this very volatility can make the desired aroma short-lived; once the fragrance composition and/or odor counteractant loading in an air freshener has been exhausted, the pleasantly scented environment dissipates and malodor, if present, returns.

Plastisols, mixtures of plasticizer and resin, commonly polyvinylchloride (PVC), are well-known in the art. Among the many uses of plastisols are coatings sealants, molded plastic parts (e.g., pipings, moldings).

Devices for dispensing volatile substances in the air through diffusion are well known in the art. U.S. Pat. No. 3,685,734 discloses a controlled fragrance release device comprising a vinyl plastisol resin containing an essential oil or other volatile substance that is bonded to a base supporting ply with a low vapor transmission rate and covered with a removable cover sheet that contains the volatile substance until removed or replaced.

U.S. Pat. No. 6,749,861 teaches an insect repellant composition comprising a high vapor pressure fragrance capable of repelling insects and a low vapor pressure non-fragrance insect repellant (e.g., DEET) which is soluble in the fragrance, and an absorption substrate carrier selected from the group consisting of paper, plastisol, gel, fabric, clay, wax, and plastic. More particularly, the '861 Patent discloses as preferred embodiments fragrance-containing PVC plastisol compositions for paper substrates. The insect repellant DEET is taught to be present in such embodiments at concentrations of up to about 80%. The maximum concentration of fragrance taught to be used in these embodiments is an amount which is soluble in the PVC plastisol and which does not destroy its film-forming properties (i.e., 1% to about 20%, most preferably about 13%). The present invention teaches fragrance concentrations in excess of about 90% for the purpose of air-freshening an environment.

A PVC resin fragrance delivery product has previously been commercialized and sold under the brand name Cool Foot by Medo Industries, Inc., now sold under the same name by SOPUS Products (Shell Oil). The Cool Foot product was based on plasticized PVC resin (powder or granule) with durometer readings of about 65 to about 80. It had fragrance loadings of less than about 20% and was meant to be free-standing (i.e., outside a package container or other supporting structure).

The fragrance delivery gel composition of the present invention differs from the commercially-available Cool Foot products in several respects, chief among which is the ability of the present invention to hold and deliver over four times the fragrance loadings in Cool Foot, while still maintaining the integrity of the gel delivery system. Another difference is that the fragrance delivery gel composition of the present invention surprisingly maintains the character of a low-viscosity, flowable liquid during the cooling phase (i.e., after reaching requisite processing temperatures or requisite re-melting temperatures). The gel composition of the present invention remains a low-viscosity, flowable liquid to temperatures as low as about 125° F.; below those temperatures, the present invention becomes a non-flowable gel. This unexpected attribute enables the gel composition of the present invention to be portioned into containers at temperatures considerably lower than original process temperatures or re-melting temperatures, thus greatly diminishing the loss of expensive fragrance into the environment during portioning operations. In contrast, the commercially-available "Cool Foot" product must be portioned by injection molding at temperatures in excess of 325° F. The "Cool Foot" product does not exist as a low-viscosity, flowable liquid below temperatures of 325° F. and, accordingly, cannot be portioned into open "containers" or by "open-mold casting. A further difference between the present invention and Cool Foot, is that the PVC resin in the prior art Cool Foot product was solid at room temperature. In contrast, the PVC resin used in the fragrance delivery system of the present invention is liquid at room temperature, thereby enabling it to be pumped as a liquid into a processing system.

It is known in the art that incorporating essential oils and/or fragrances into plasticized PVC in order to produce gelled fragrance compositions requires application of heat at temperatures in excess of at least about 285° F. It is also known in the art that essential oils and/or fragrances are sensitive to heat and other environmental stressors. Accordingly, there exists a long-felt but as yet unmet need for a process to manufacture plasticized PVC gelled perfumery materials that minimizes, and ideally eliminates, loss of essential oils and/or perfumery materials due to heat and other environmental stressors during the manufacturing process. The highly efficient, closed-loop manufacturing process of the present invention meets these needs. By limiting the processing time at requisite elevated temperatures, the present invention maximally maintains the concentration and integrity of the essential oils and other aroma-producing materials.

The manufacturing process of the present invention also provides economic benefits by maximizing the concentration of expensive fragrance ingredients in the post-processed finished gel composition. The thermal reversibility of the gel compositions of the present invention provides yet another economic advantage. Temperatures of at least about 285° F. are not needed to thermally reverse the gel of the present invention. Rather, lower temperatures of less than about 200° F. are sufficient to thermally reverse gel of the present invention. This attribute allows compositions of the present invention to be shipped in bulk to distribution centers for portioning and packaging. Further, during portioning and packaging, steam heat (i.e., less than about 200° F.) may be used to thermally reverse gels of the present invention. Additionally, the gel composition of the present invention can be re-melted and thereafter portioned into containers as a low-viscosity, flowable liquid to temperatures as low as about 125° F. As used in the present invention the phrase "thermally reversible" means that the aroma-releasing polymeric gel matrix of the present invention can be re-melted at temperatures from about 125° F. to less than about 200° F. and then portioned (i.e., from a drum or pail into small containers) as a low-viscosity, flowable liquid. When the portioned, low-viscosity, flowable liquid cools, it reconstitutes into a non-flowable gel. The high loadings of fragrance and/or odor-counteractants confer additional advantages including increased product life and/or reduced product physical size as well as cost reductions (in terms of packaging, transportation and logistics costs, and retail (on shelf) space). Additionally, reduced packaging produces less post consumer waste.

In addition to achieving loadings of fragrance and/or odor-counteractants up to about 96% by weight of the total composition, and the ability to deliver those loadings at a persistent rate over a prolonged period of time, the present invention meets the long-felt but unmet need for a long-acting aroma delivery matrix with exceptional clarity. As used in the present invention the phrase "long-acting" and/or "long-lasting" means gels that exude a discernable aroma in excess of 30 days, preferably in excess of 60 days and most preferably in excess of 90 days. The clear to translucent gels of the present invention can also be made in a wide range of colors through the addition of dyes and other colorants and/or opacifiers. Another aesthetic need that is met by the present invention is the ability to suspend three-dimensional decorative items, including, but not limited to, colored pigments, glitters and other small, decorative objects (e.g., figurines, artificial flowers).

SUMMARY OF THE INVENTION

The present invention relates to a translucent-to-clear, plasticized PVC thermoplastic polymeric matrix gel composition comprising: (i) a high loading of fragrance composition and/or odor counteractant(s)—preferably greater than about 85%; (ii) from about 4% to about 25% of a plastisol with a Shore hardness of from about 60 to about 95 that is liquid at room temperature; and, optionally, (iii) an evaporation/firmness controlling agent. The high loading of fragrance and/or odor counteractants in the polymeric matrix gel composition of the present invention provides a desired aroma to an environment in a persistent manner over a period of time greater than has been heretofore possible in polymeric fragrance gel matrix systems.

DETAILED DESCRIPTION OF THE INVENTION

One aspect, the present invention relates to a translucent-to-clear, PVC thermoplastic polymeric matrix gel composition comprising: (i) greater than about 80% of a fragrance composition and/or odor counteractants; (ii) from about 4% to about 25% of a PVC; and, optionally, (iii) an evaporation/firmness controlling agent.

Another aspect of the present invention relates to a translucent-to-clear plasticized PVC thermoplastic polymeric matrix gel composition comprising: (i) greater than about 80% of a fragrance composition and/or odor counteractants; (ii) from about 4% to about 25% of a PVC plastisol having a Shore hardness of from about 60 to about 95 that is liquid at room temperature; and optionally, (iii) an evaporation/firmness controlling agent.

In a further aspect of the invention a long-lasting aroma is imparted to an environment in a persistent manner from a translucent-to-clear, plasticized PVC thermoplastic polymeric matrix gel composition comprising: (i) greater than about 80% of a fragrance composition and/or odor counteractants; (ii) from about 4% to about 25% of a plastisol having a Shore hardness of from about 60 to about 95 that is liquid at room temperature; and, optionally, (iii) an evaporation/firmness controlling agent.

Plastisol

The use of non-plasticized PVC resin(s) in the manufacture of high-concentration air freshener gels subject of the present invention was heretofore unknown. Geon 138 from PolyOne (Avon Lake, Ohio) is an example of such a non-plasticized plasticized PVC resin suitable for use in the present invention. Applicants have found that special care must be taken to assure that the dry resin and fragrance to be gelled therein have been thoroughly homogenized (e.g., no settling, no separation, no clumping, ect.) to allow for a uniform gel matrix.

According to a preferred aspect of the present invention, the PVC resin is plasticized. Such a mixture of PVC resin and plasticizer is referred to as a PVC plastisol or as plasticized PVC and is preferred because it produces a homogenous mixture composition. By selecting a polymer matrix that is sufficiently plasticized, a gel matrix can be processed as a liquid while at the same time maintaining a high loading of fragrance and remaining sufficiently porous to allow for the intended fragrance to migrate from the highly fragrance loaded gel reservoir in a persistent manner to the environment. A matrix with these attributes—as achieved by the present invention—provides persistant, long-acting delivery of the scent intended by the perfumer over an extended period of time, thus meeting consumer expectations from the standpoint of delivering and/or creating a consistently fragranced environment.

Plasticized PVCs useful in the present invention are selected from the group consisting of vinyl chloride homopolymer and vinyl chloride: vinyl acetate co-polymer. They have a Shore hardness of from about 60 to about 95, preferably about 85. Representative PVC plastisols meeting these criteria include the following:

| Example | Chemical Name | Tradename | Supplier |
|---------|---------------|-----------|----------|
| 1 | Polyvinyl Chloride Plastisol | E-85 | Indusol (Sutton, MA) |
| 2 | Polyvinyl Chloride Plastisol | E-95 | Indusol |
| 3 | Polyvinyl Chloride Plastisol | IF-95 | Indusol |
| 4 | Polyvinyl Chloride Plastisol | Clear Casting Plastisol (85-D) | Chemionics (Tallmadge, OH) |
| 5 | Polyvinyl Chloride Plastisol | Clear Casting Plastisol (95-D) | Chemionics |

Aroma-releasing polymeric gel matrices according to the present invention contain PVC plastisols at concentrations of from about 4% to about 25% weight/weight, preferably from about 6% to about 15% weight/weight, and most preferably from about 8% to about 12%.

Evaporation and/or Firmness Controlling Agent(s)

Optionally, the aroma-releasing polymeric gel matrices of the present invention may contain one or more additional materials that control evaporation and/or firmness of the polymeric gel matrix—Evaporation and/or Firmness Controlling Agent (EFCA). These optional materials may be present up to about 96%, preferably up to about 47%, and most preferably up to about 4%.

EFCAs useful in the present invention include, but are not limited to, the following esters: acetates, adipates, azeleates, benzoates, caprylamides, capramides, caprates, citrates, cocoates, fumarates, glutarates, glycolates, heptanoates, isobutyrates, isophthalates, laurates, linoleates, maleates, mellitates, myristates (e.g., isopropyl myristate), octanoates, oleates, palmitates (e.g. isopropyl palmitate), pelargonates, phosphates, phthalates, ricinoleates, sebacates, stearates, succinates, toluates, toluamides, tallates and decanoates. Other EFCAs suitable for use in the present invention include diproplylene glycol, hexylene glycol, isoparafinic hydrocarbons, including those sold under the tradename Isopar M by ExxonMobil (Houston, Tex.), polymeric PVC plasticizers, including those sold under the Tradename Admex by Velsicol Chemical Corp. (Rosemont, Ill.), and odorless mineral spirits.

Particularly preferred EFCAs according to the present invention and commercial sources from which they are available are listed in the table below:

| Example | Chemical | Supplier |
|---------|----------|----------|
| 6 | Benzyl benzoate | Andrea Aromatics (Trenton, NJ) |
| 7 | Di-2-ethylhexyl phthalate | Chemionics |
| 8 | Proprietary blend of esters and phthalates | Andrea Aromatics |
| 9 | Diethyl phthalate | Andrea Aromatics |
| 10 | Dioctyl terephthalate | Andrea Aromatics |
| 11 | Dioctyl adipate | Andrea Aromatics |
| 12 | Hexanedioic acid polymer with 1,4-butanediol and 1,2-propanediol didecanoate | Velsicol Chemical Corp. |
| 13 | Benzyl3-isobutyryloxy-1-isopropyl-2,2-dimethyl-propyl phthalate | Ferro Corp. (Bridgeport, NJ) |

Fragrance Compositions/Odor Counteractants

A distinct, ambient aroma—one possessing a desired, recognizable character—is achieved by blending perfumery materials of defined quality in specified proportions. Perfumery materials include essential oils, concretes and extracts and aroma-producing chemicals, which may be of natural or synthetic origin. As used in the present application, the term "fragrance composition" refers to a blend of perfumery ingrediants with a characteristic odor or "note". More particularly, fragrance compositions are made up of "accords"—mixtures of two or more perfumery materials having a unified olfactory theme.

Sources of natural fragrance ingredients include: blossoms; leaves and stems; fruit peels; seeds; roots; woods; herbs; needles and branches; resins and balsams; and lichens. Natural ingredients are obtained by techniques that are well-known to those of skill in the art—essential oils by steam distillation or crushing; concretes by extraction with volatile solvents; absolutes by extraction of concretes with alcohol.

Representative, non-limiting examples of essential oils suitable for use in fragrance compositions delivered by the gel matrix of the present invention include cedarwood, cinnamon, frankincense, mimosa, narcissus, neroli, patchouli, rosewood, sandalwood, tagetes, vanilla, vetiver, violet, and YlangYlang. Diluents well-known to those of skill in the art may be used in combination with essential oils.

As used in the present application, the term "fragrance composition" refers to a blend of individual perfumery materials, The individual perfumery materials and accords suitable for use in the delivery system of the present invention are catalogued and described in references and databases well-known to those of skill in the art including the following: S. Arctander, Perfume and Flavor Chemicals, Volumes I & II (1960, 1969; reprinted 2000); Allured's Flavor and Fragrance Materials (2005); the database maintained by the Research Institute for Fragrance Materials at www.rifm.org. Representative examples of fragrance compositions useful in the present invention and sources from which they are available are listed in the table below:

| Example | Fragrance | Source |
|---------|-----------|--------|
| 14 | Mango | Andrea Aromatics |
| 15 | Spiced Apple | Wessel Fragrances (Englewood Cliffs, NJ) |
| 16 | Delicious Apple | Andrea Aromatics |
| 17 | Mulberry | Andrea Aromatics |
| 18 | Pine Powerhouse | Andrea Aromatics |
| 19 | Ocean Mist | Symrise (Teterboro, NJ) |
| 20 | Bubble Gum | Andrea Aromatics |

The term "odor counteractant" as used in the present invention means a chemical that reacts with or neutralizes a malodor. Odor counteractants are articles of commerce well-known to those of skill in the art. Representative examples of odor-counteractants and commercial sources from which they are available include the following:

| Example | Chemical Name | Tradename | Supplier |
|---------|---------------|-----------|----------|
| 21 | Aldehyde | Deodorizer Aldehyde, INA | Andrea Aromatics |

Fragrance composition and/or odor-counteractant(s) are present in the polmeric gel matrices of the present invention at concentrations of from greater than about 80%. Preferably, volatile fragrances are present at concentrations of from greater than about 85%; more preferably, volatile fragrances are present at concentrations of from about 85% to about 94%; still more preferably at concentrations of from about 88% to about 92%. Fragrance and/or odor counteractant can be loaded into the polymeric gel matrices of the present invention at concentrations up to about 96% by weight of the total composition.

Compositions of the present invention may be housed in a container suitable for housing air-freshener compositions. The container may be made of glass, plastic, ceramic, wood, paper or metal or other materials known to those of skill in the art. Compositions of the present invention may be used in static, forced air (fan unit, filtration unit, HVAC system) and thermal (heat) air-freshener applications. Non-limiting examples of environments where air freshening is desirable include restrooms, homes, automobiles, commercial vehicles including buses and tractor-trailers, commercial and private boats, recreational vehicles, campers, commercial and private aircraft, retail business, commercial office space, and portable toilets.

EXAMPLES

Compositions of the present invention are made by the following process. Mix the specified grams of PVC plastisols (Examples 1-5) with the specified grams of fragrance components (Examples 14-20) and/or odor counteractants (Example 21) and, optionally, the specified grams of ECFA (Examples 6-13) thoroughly and continuously with medium propeller agitator without forming a vortex and via tank recirculation for duration of processing. Pump the homogenously mixed material through a closed loop, heat exchanger at temperatures of from about 280° F. to about 330° F. Preferably the components of the closed loop system are non-ferrous or stainless steel to prevent fragrance adulteration. Residence time during the heating phase is limited to from about 30 to about 60 seconds. Upon exiting the heating-phase, heat exchanger, material is pumped directly into a closed-loop, cool-down phase heat exchanger for about 30 to about 60 seconds; there the temperature is reduced to a portioning temperature of from about 130° F. to about 200° F. The resulting material is portioned and/or filled into appropriate containers or bulk drums

| Example | PVC Plastisol Example | Wt % | Fragrance/ Counteractant Example | Wt % | EFCA Example | Wt % |
|---|---|---|---|---|---|---|
| 19 | 4 | 8.9 | 14 | 0.1 | 6; 7 | 91.0 |
| 20 | 4 | 25.0 | 15 | 75.0 | N/A | 0.0 |
| 21 | 4 | 4.0 | 16 | 96.0 | N/A | 0.0 |
| 22 | 4 | 8.9% | 14 | 0.1% | 6&7 | 91.0% |
| 23 | 4 | 25.0% | 15 | 75.0% | n/a | 0.0% |
| 24 | 4 | 4.0% | 16 | 96.0% | n/a | 0.0% |
| 25 | 4 | 4.0% | 16 | 0.1% | 7 | 95.9% |
| 26 | 4 | 8.0% | 21 | 5.0% | 7 | 87.0% |
| 27 | 4 | 8.0% | 17 | 46.0% | 11 | 46.0% |
| 28 | 4 | 8.0% | 17 | 46.0% | 10 | 46.0% |
| 29 | 2 | 8.0% | 18 | 92.0% | n/a | 0.0% |
| 30 | 4 | 6.0% | 19 | 94.0% | n/a | 0.0% |
| 31 | 4 | 8.0% | 20 | 87.0% | 12 | 5.0% |
| 32 | 4 | 8.0% | 20 | 87.0% | 13 | 5.0% |

The above-described procedure was repeated by substituting 5.0% of a non-plasticized PVC resin (Geon 138) for a plastisol and combining it with 95.0% Spiced Apple fragrance (Wessel Fragrances).

While the illustrative embodiments of the invention have been described with particularly, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A thermally-reversible, aroma-releasing PVC thermoplastic polymeric matrix gel composition made by the process comprising the steps of:
   (a) a first step of creating a homogenous liquid solution comprising
      (i) greater than 80% weight/weight of a fragrance composition and/or odor counteractants;
      (ii) from about 4% to about 25% weight/weight of a PVC; and
      (iii) optionally, an Evaporation/Firmness Controlling Agent wherein the fragrance composition and/or odor counteractants, the PVC and, optionally, the Evaporation/Firmness Controlling Agent are mixed together until homogenous; followed by
   (b) a second step wherein the homogenous liquid solution from step (a) is heated by pumping through a first closed-loop heat exchanger to a temperature of from about 280° F. to about 330° F.; followed by
   (c) a third step wherein the homogenous liquid solution from step (b) is cooled by pumping through a second closed-loop heat exchanger to a temperature of from about 130° F. to about 200° F., thereby forming a thermally-reversible, aroma-releasing PVC thermoplastic polymeric matrix gel composition.

2. A composition according to claim 1 that has a translucent or clear appearance.

3. A composition according to claim 1 where the fragrance composition and/or odor counteractant is present at a concentration of greater than 85% weight/weight.

4. A composition according to claim 1 where the fragrance composition and/or odor counteractant is present at a concentration of from about 85% to about 96% weight/weight.

5. A composition according to claim 1 where the fragrance composition and/or odor counteractant is present at a concentration of from about 88% to about 92% weight/weight.

6. A composition according to claim 1 where the Evaporation/Firmness Controlling Agent is present at a concentration of up to about 47% weight/weight.

7. A composition according to claim 1 where the Evaporation/Firmness Controlling Agent is present at a concentration of up to about 4% weight/weight.

8. A composition according to claim 1 where the Evaporation/Firmness Controlling Agent is selected from the group consisting of esters of phthalic acid, esters of benzoic acid, esters of adipic acid, and polymeric PVC plasticizers.

9. A composition according to claim 8 where the ester of phthalic acid is selected from the group consisting of di-2-ethylhexyl phthalate, dioctyl terephthalate, diethyl phthalate, Benzyl 3-isobutyryloxy-1-isopropyl-2,2-dimethyl-propyl phthalate.

10. A composition according to claim 8 where the ester of benzoic acid is benzyl benzoate.

11. A composition according to claim 8 where the ester of adipic acid is dioctyl adipate.

12. A composition according to claim 8 where the polymeric PVC plasticizer is a mixture of Hexanedioic acid polymer, 1,4-butanediol and 1,2-propanediol didecanoate.

13. A composition according to claim 1 where the fragrance component is comprised of one or more perfumery materials selected from the group consisting of essential oils, concretes, extracts and aroma-producing chemicals.

14. A composition according to claim 13 where the fragrance component is comprised of one or more essential oils.

15. A composition according to claim 1 where the odor counteractant is aldehydic.

16. A thermally-reversible, aroma-releasing PVC thermoplastic polymeric matrix gel composition made by the process of
    (a) a first step of creating a homogenous liquid solution comprising
        (i) greater than about 80% weight/weight of a fragrance composition and/or odor counteractants;
        (ii) from about 4% to about 25% weight/weight of a PVC plastisol; and,
        (iii) optionally, an Evaporation/Firmness Controlling Agent wherein the fragrance composition and/or odor counteractants, the PVC plastisol and, optionally, the Evaporation/Firmness Controlling Agent are mixed together until homogenous; followed by
    (b) pumping the homogenous liquid solution from step (a) through a first closed-loop heat exchanger to heat the homogeneous solution to a temperature of from about 280° F. to about 330° F.;
    (c) pumping the liquid solution from step (b) through a second closed-loop heat exchanger to cool the liquid solution from step (b) to a temperature of from about 130° F. to about 200° F., thereby forming a thermally-reversible, aroma-releasing PVC thermoplastic polymeric matrix gel composition.

17. A composition according to claim 16 that has a translucent appearance.

18. A composition according to claim 16 that has a clear appearance.

19. A composition according to claim 16 where the fragrance composition and/or odor counteractant is present at a concentration of greater than about 85% weight/weight.

20. A composition according to claim 16 where the fragrance composition and/or odor counteractant is present at a concentration of from about 85% to about 96% weight/weight.

21. A composition according to claim 16 where the fragrance composition and/or odor counteractant is present at a concentration of from about 88% to about 92% weight/weight.

22. A composition according to claim 16 where the plastisol has a Shore hardness of about 85 that is liquid at room temperature.

23. A composition according to claim 16 where the plastisol is selected from the group consisting of vinyl chloride homopolymer and vinyl chloride: vinyl acetate co-polymer.

24. A composition according to claim 16 where the plastisol is present at from about 6% to about 15% weight/weight.

25. A composition according to claim 16 where the plastisol is present at from about 8% to about 12%.

26. A composition according to claim 16 where the Evaporation/Firmness Controlling Agent is present at a concentration of up to about 47% weight/weight.

27. A composition according to claim 16 where the Evaporation/Firmness Controlling Agent is present at a concentration of up to about 4% weight/weight.

28. A composition according to claim 16 where the Evaporation/Firmness Controlling Agent is selected from the group consisting of esters of phthalic acid, esters of benzoic acid, esters of adipic acid, and polymeric PVC plasticizers.

29. A composition according to claim 28 where the ester of phthalic acid is selected from the group consisting of di-2-ethylhexyl phthalate, dioctyl terephthalate, diethyl phthalate, Benzyl 3-isobutyryloxy-1-isopropyl-2,2-dimethyl-propyl phthalate.

30. A composition according to claim 28 where the ester of benzoic acid is benzyl benzoate.

31. A composition according to claim 28 where the ester of adipic acid is dioctyl adipate.

32. A composition according to claim 28 where the polymeric PVC plasticizer is a mixture of Hexanedioic acid polymer, 1,4-butanediol and 1,2-propanediol didecanoate.

33. A composition according to claim 16 where the fragrance component is comprised of one or more perfumery materials selected from the group consisting of essential oils, concretes, extracts and aroma-producing chemicals.

34. A composition according to claim 33 where the fragrance component is comprised of one or more essential oils.

35. A composition according to claim 16 where the odor counteractant is aldehydic.

\* \* \* \* \*